United States Patent [19]

Ness

[11] Patent Number: 4,629,457
[45] Date of Patent: Dec. 16, 1986

[54] ABSORBENT FACING AND METHOD FOR MAKING THE SAME

[75] Inventor: Irving S. Ness, Hilton Head Island, S.C.

[73] Assignee: Chicopee, New Brunswick, N.J.

[21] Appl. No.: 783,289

[22] Filed: Oct. 2, 1985

Related U.S. Application Data

[60] Division of Ser. No. 579,939, Feb. 14, 1984, abandoned, and a continuation-in-part of Ser. No. 507,906, Jun. 27, 1983, abandoned, which is a continuation of Ser. No. 917,696, Jun. 21, 1978, abandoned.

[51] Int. Cl.⁴ .............................................. A61F 13/16
[52] U.S. Cl. ..................................... 604/382; 604/370
[58] Field of Search ............... 604/372, 370, 378, 380, 604/382; 128/155, 156; 428/195, 245

[56] References Cited

U.S. PATENT DOCUMENTS

| | | | |
|---|---|---|---|
| 2,862,251 | 12/1958 | Kalwaites | 128/290 |
| 3,221,738 | 12/1965 | EkBerg et al. | 128/287 |
| 3,307,545 | 3/1967 | Surowitz | 128/156 |
| 3,331,728 | 7/1967 | Lane | 128/156 |
| 3,441,021 | 4/1969 | Endres | 128/156 |
| 3,825,007 | 7/1974 | Rand | 128/296 |
| 3,888,248 | 6/1975 | Moore et al. | 128/156 |
| 3,911,186 | 10/1975 | Trotman | 428/245 |
| 3,994,299 | 11/1976 | Rarami | 128/287 |
| 4,115,176 | 9/1978 | Ekstand | 428/195 |
| 5,703,897 | 11/1972 | Mack et al. | 128/156 |

*Primary Examiner*—C. Fred Rosenbaum
*Assistant Examiner*—S. Vinyard
*Attorney, Agent, or Firm*—Nancy A. Bird

[57] ABSTRACT

An absorbent facing is disclosed which has significant one-way valve characteristics for aqueous fluids. The facing is produced by a process which comprises the steps of: (a) superimposing a thin polymer film and a first web comprising absorbent fibers, to form a second web; (b) heating the second web to a temperature such that the polymer film is in a formable state; (c) while the said second web is so heated, simultaneously applying shearing and compressive forces to the second web to form said polymer film into a coating on said first web, the coating comprising a fine pattern of continuous areas which lie between and interconnect discontinuous areas, wherein the polymer in the continuous areas comprises a continuous or substantially continuous coating on the surface of said first web, and wherein most of the polymer in the discontinuous areas is coated on individual fibers; and (d) cooling the coated web thus formed to cool the polymer below its forming temperature.

15 Claims, 15 Drawing Figures

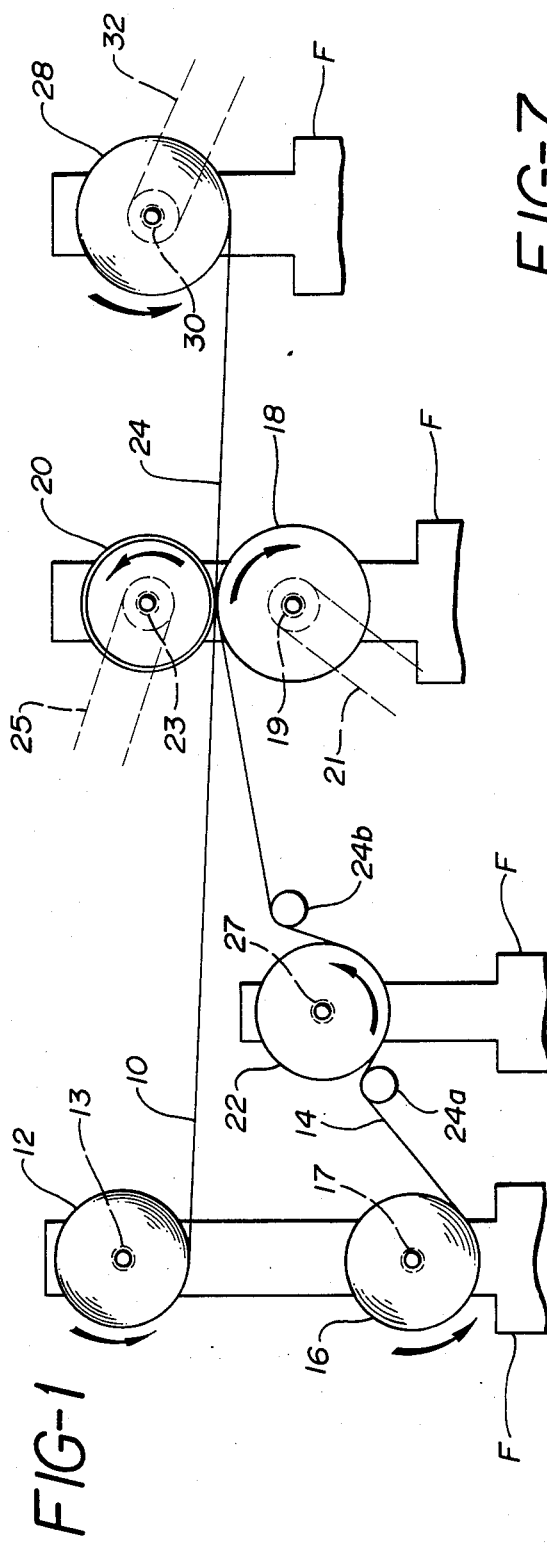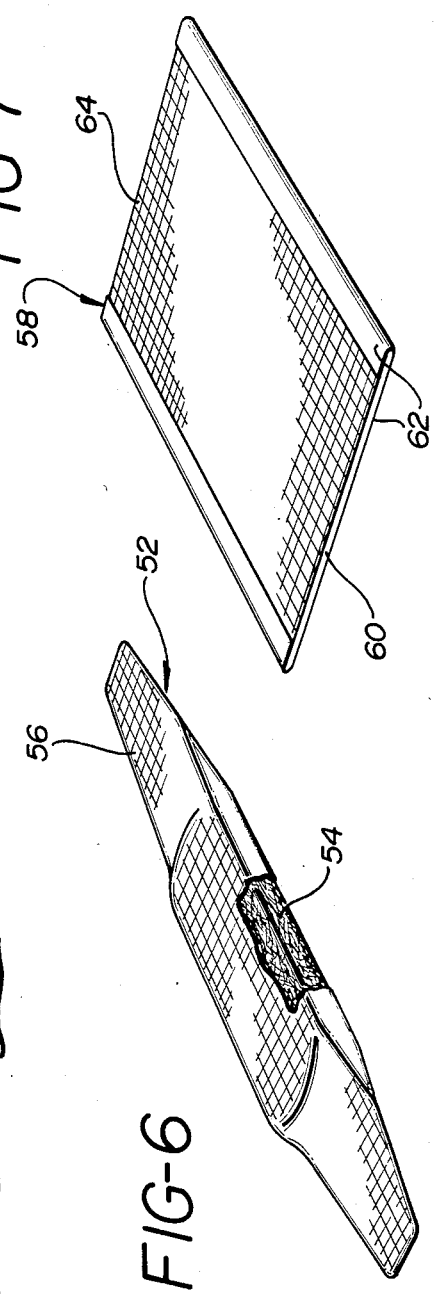

ABSORBENT FACING AND METHOD FOR MAKING THE SAME

This is a division of application Ser. No. 579,939 filed Feb. 14, 1984, now abandoned, and this is a continuation-in-part of application Ser. No. 507,906 filed June 27, 1983, now abandoned, which is a continuation of Ser. No. 917,696 filed June 21, 1978, now abandoned.

The invention relates to an absorbent facing and to a process for producing the same.

FIELD OF THE INVENTION

Absorbent facings are often employed in such articles as disposable diapers, dressings, bandages, incontinent pads, sanitary products, and the like. An ideal absorbent facing would permit liquid to pass through it from a source to the absorbent material behind the facing, but would prevent liquid from flowing in the reverse direction. To state this desirable property in another way, it would be desirable to have an absorbent facing exhibit "one-way valve" characteristics to aqueous liquids.

DESCRIPTION OF THE PRIOR ART

A number of approaches have been employed to impart one-way valve characteristics to the facings of absorbent materials. One such method is described by Kozak, in U.S. Pat. No. 3,814,101, in which the absorbent material is faced with a polymeric film having a repeating pattern of indentations or dimples and slits in the film.

In Surowitz, U.S. Pat. No. 3,307,545, a non-adherent dressing is described in which an absorbent material is faced with a polymer film having a pattern of depressions therein, with the depressions having openings to the absorbent material. The stated purpose of the facing of Surowitz is to prevent a dressing from adhering to a wound.

Canadian Patent No. 731,336 discloses a diaper or similar protective garment having a plastic sheet facing for an absorbent core, said facing having a plurality of spaced apart regions, each of which is rendered liquid-permeable by a plurality of minute perforations therein.

SUMMARY OF THE INVENTION

Broadly, the process for producing an absorbent facing material that is provided by this invention comprises the steps of:

(a) superimposing a thin polymer film and a first web comprising absorbent fibers, to form a second web having said thin polymer film on one face and said first web on the other face;

(b) heating said second web to a temperature such that said polymer film is formable;

(c) while said second web is so heated, simultaneously applying shearing and compressive forces to said second web to form said polymer film into a coating on said first web, said coating comprising a fine pattern of continuous areas which lie between and interconnect discontinuous areas, wherein the polymer in the continuous areas comprises a continuous or substantially continuous coating on the surface of said first web, and wherein most of the polymer in the discontinuous areas is coated on individual fibers; and (d) cooling the coated web thus formed to cool the polymer below its forming temperature.

BRIEF DESCRIPTION OF THE DRAWINGS

FIG. 1 is a schematic view in elevation of one type of apparatus that can be employed to carry out the process of the invention;

FIG. 6 is a perspective view of a sanitary napkin which utilizes the absorbent facing material of the invention;

FIG. 7 is a perspective view of a disposable diaper which utilizes the absorbent facing material of the invention;

DESCRIPTION OF THE PREFERRED EMBODIMENTS

Figure 2:
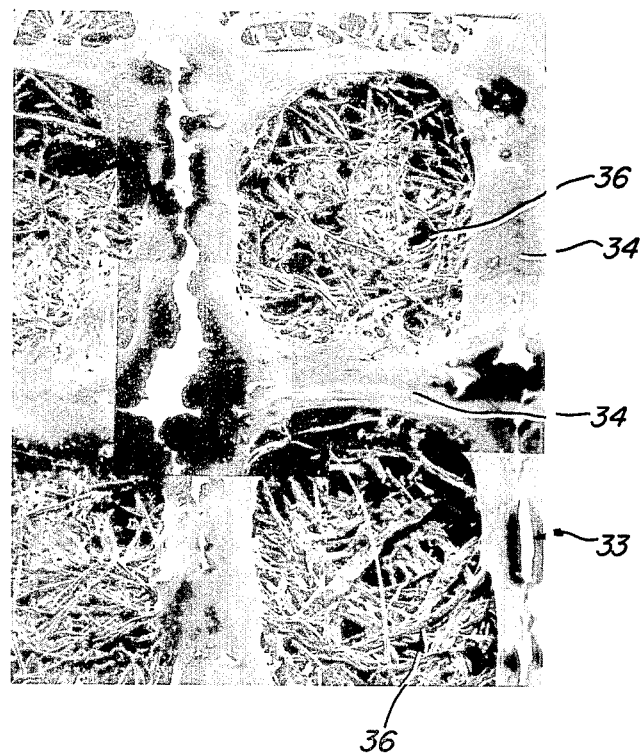
FIG. 2 is a scanning electron micrograph of one type of absorbent facing material of the invention shown at a magnification of 75×.

Referring to FIG. 1, there is shown an apparatus that can be employed to carry out the process of the invention. In carrying out the process, a polymer film 10 and a fibrous web 14 composed principally of absorbent fibers are taken off suitable supply rolls 12, 16, which are mounted for rotation on bearings 13, 17 mounted in suitable framing F. The film 10 and fibrous web 14 are superimposed and are passed through the nip of a pair of counter-rotating rolls 18, 20. The rolls are mounted for rotation on bearings 19, 23 mounted in suitable framing F, and are driven by suitable drive mechanisms 21, 25. The bottom roll 18 that is in contact with the fibrous web 14 has a smooth, uniform surface. Said bottom roll 18 is heated. The top roll 20 that is in contact with the polymer film 10 has a resilient surface that has a pattern of continuously arranged recessed areas (grooves) and discontinuously arranged raised areas disposed uniformly over the surface of the roll 20. As a general rule, the grooves will usually be from about 0.002 inch to about 0.05 inch wide, and from about 0.001 inch to about 0.035 inch deep. Preferably, the resilient roll 20 is moving at a peripheral speed slightly higher than the peripheral speed of the smooth roll 18. Peripheral speed ratios of from about 1.1:1 to 1.5:1 are suitable. After passing through the nip of the rolls 18, 20, the polymer film is formed into a coating on the fibrous web, with the coating comprising a fine pattern of continuous areas which lie between and interconnect discontinuous areas, wherein the polymer in the continuous areas comprises a continuous or substantially continuous coating on the surface of the fibrous web, and wherein the polymer in the discontinuous areas is coated on individual fibers.

The apparatus that can be employed to carry out the process of this invention is similar to the apparatus disclosed by Kalwaites, in U.S. Pat. No. 3,881,381.

A wide variety of thin films can be employed in the invention. The preferred films are made from olefin polymers, such as polyethylene, both high and low density, polypropylene, ethylene copolymers such as ethylene/vinyl acetance, ethylene/ethyl acrylate, and others such as ethylene/methyl acrylate. It is desirable to employ a film having a thickness of from about ¼ mil to about 1 ¼ mils. In one preferred aspect, a corona-treated polyethylene film is used in order to achieve improved adhesion between the film and the fibrous web.

The fibrous web employed in the invention is composed predominantly of absorbent fibers. (By "absorbent fibers" is meant those fibers that have an affinity for aqueous liquids.) The web can contain cellulosic fibers such as wood pulp, cotton, and rayon, or other hydrophilic fibers such as polyvinyl alcohol fibers or normally hydrophobic fibers such as polyester or polypropylene that have been treated by known methods to make them hydrophilic. It is generally preferred that the web be composed mostly of short or papermaking fibers, although textile length fibers can be employed. Minor amounts of non-absorbent fibers can be employed if desired. The web can be a loosely formed dry laid product, or it can be wet laid. If desired, the fibrous web can be lightly bonded. The binder can be viscose or other hydrophilic binder, it can be an acrylic binder, polyvinyl acetate, ethylene-vinyl acetate copolymer, SBR rubber, or the like. If desired, the binder can be cross-linkable. The binders that can be employed are well-known in the art. The web can be overall saturated with binder, or it can be print or spot bonded. The web can contain a small proportion of thermoplastic fibers, which can be used as binding means by calendering, or the like. While it is generally preferred to employ rather light weight webs (of the order of ½ to 2 ½ ounces per square yard), the invention can be employed with heavier webs.

The temperature of the heated roll 18 is sufficient to increase the temperature of the film 10 to at least the forming temperature of the polymer in the film 10. The precise temperature employed in particular cases will depend upon factors such as the nature of the polymer in the film 10, the speed of the webs in passing through the nip, the thickness or weight of the fibrous web 14, the pattern of engraving on the resilient roll 20, and similar factors. As an illustration, when ½ mil low density polyethylene film is employed, the peripheral speed of the smooth roll 18 is about 6 feet per minute, and the peripheral speed of the resilient roll 20 is about 8 feet per minute, a temperature of from about 260° to about 390° F. in the smooth roll 18 has been found to be useful. Preferably, the temperature in the smooth roll 18 is from about 275° to about 370° F. in this case.

The resilient roll 20 is usually at a temperature below the forming temperature of the polymer in the film 10. Again, this will vary from one polymer to another, speed of the web, and the like, but for the conditions stated above using the ½ mil polyethylene film and the speeds stated above, a temperature in the resilient roll 20 of from about 150° to about 220° F. has been found useful. Preferably, the temperature in the resilient roll 20 is from about 170° to 215° F. for these conditions.

As is seen from the breadth of the temperature ranges indicated above, the exact temperature employed has not been found to be narrowly critical. The important factors are to heat the film to its forming temperature, and to avoid sticking of the film to the resilient roll. It is well within the ordinary skill of the art to determine optimum temperatures in particular cases.

The resilient roll will ordinarily have a Durometer Shore A hardness of from about 45 to about 90. The surface of this roll can be of rubber; either hydrocarbon rubber or silicone rubber would be suitable. The surface of the resilient roll is engraved with a regular pattern of lines. As a general rule, the engraved pattern would be such as to provide from about 100 to about 10,000 openings (i.e., raised areas) per square inch of surface.

Pressure is maintained on the two rolls 18, 20 in order to provide a pressure at the nip of from about 5 to about 90 pounds per linear inch. The pressure can be provided by suitable hydraulic means such as those that are well known in the art.

After the coated web 26 passes through the nip of the rolls 18, 20, the polymer coating cools below the forming temperature of the polymer.

The coated web 26 is collected on a suitable wind-up 28, that is mounted for rotation on bearings 30 mounted on suitable framing F, and driven by a suitable drive mechanism 32.

In some cases, such as when operating at relatively high speeds, it may be desirable to preheat the fibrous web 14. This can be done by passing the web 14 around a preheating roll 22, which is mounted for rotation on bearings 27 mounted on suitable framing F. The web 14 passes around idler rolls 24a, 24b before and after the preheating roll 22.

The invention is further illustrated by the following examples:

EXAMPLE 1

Using an apparatus substantially as shown in FIG. 1 (without the preheating roll), an absorbent facing was made from ½ mil polyethylene film (density: 0.92 to 0.923, melt index: 5 to 7) and a fibrous web composed of 75 weight percent wood pulp ("Alphanier F", from the Rayonier Corporation) and 25 weight percent rayon (1-9/16 inch, 1.5 denier), overall saturation bonded with Hycar 2600×120 (an acrylic latex containing a small amount of polymerized N-methylolacrylamide cross-linker). The web weighed about 1 ¼ ounces per square yard, and was made in accordance with the procedure described in Example IV of Liloia et al, U.S. Pat. No. 3,663,348.

The resilient roll had a silicone rubber surface with a Durometer Shore A hardness of about 60, and was engraved with a continuous pattern of recessed lines 0.020 inch wide and 0.018 inch deep, with 16 lines per inch running in the longitudinal direction (i.e., parallel to the longitudinal axis of the roll) and 20 lines per inch in the transverse direction. The smooth roll had a steel surface. The surface of the smooth roll was maintained at about 285° F., and the surface of the resilient roll reached an equilibrium temperature of about 180° F., by appropriate heat exchange means. The pressure at the nip was about 40 pounds per linear inch. The periphery of the smooth roll was moving at a speed of 6 feet per minute, and the periphery of the resilient roll was moving at a speed of 8 feet per minute.

A scanning electron micrograph (at about 75×) of the absorbent facing made in this Example 1 is shown in FIG. 2. The absorbent facing product 33 has a fine pattern of continuous areas 34 wherein the polyethylene is present as a continuous coating on the surface of the web. These continuous areas 34 correspond to the pattern of recessed lines engraved on the surface of the resilient roll. In between the continuous areas 34 are discontinuous areas 36 wherein most of the polyethylene is present as a coating on individual fibers.

Aqueous fluids readily pass through the coated surface of this absorbent facing product 33 to the absorbent fibers beneath the surface, but the fluids do not readily flow in the reverse direction.

EXAMPLE 2

Figure 3:
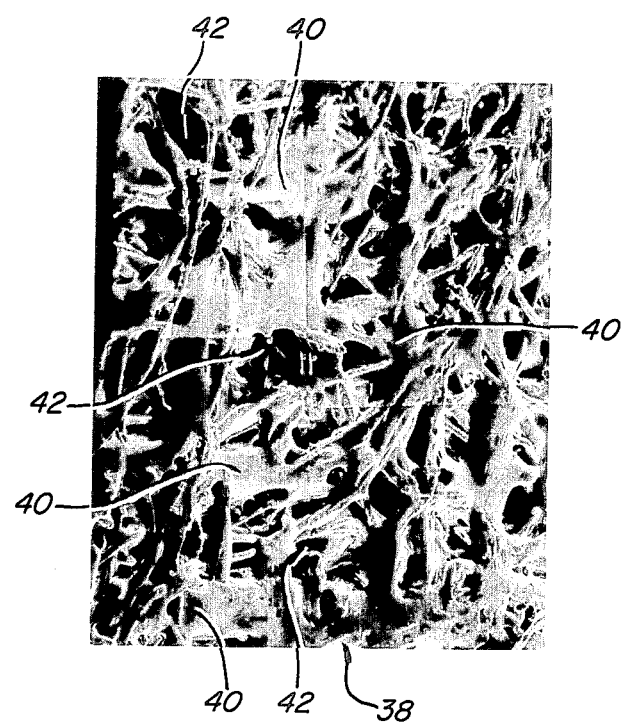
FIG. 3 is a scanning electron micrograph of another type of absorbent facing material of the invention, shown at a magnification of 140×.

An absorbent facing was made using the same materials as those described in Example 1, and using substantially the same procedure except that the resilient roll had a pattern of 100 recessed lines per inch engraved in both the longitudinal and transverse directions. The lines were 0.00255 inch wide and 0.00118 inch deep. The surface temperature of the heated smooth roll was about 360° F., and the resilient roll had a surface temperature of about 200° F. A scanning electron micrograph (at about 140×) of the absorbent facing product 38 is shown in FIG. 3. The product 38 has a fine pattern of continuous areas 40 in which the polyethylene is present as a substantially continuous coating on the surface of the web. These continuous areas 40 correspond to the pattern of engraved recessed lines on the surface of the resilient roll. In between the continuous areas 40 are discontinuous areas 42 in which most of the polyethylene is coated on the surface of individual fibers Aqueous liquids readily flow through this absorbent facing from the polymer-coated side, but do not readily flow in the reverse direction.

CONTROL EXAMPLE 1

The process of Example 1 was repeated except that the resilient roll employed had a smooth surface. The resulting product was simply a web of fibers having a continuous film of polyethylene loosely adhered to the surface thereof. Thus, the surface could not be penetrated by aqueous liquids.

CONTROL EXAMPLE 2

When an open net of polyethylene is calendered to the surface of the fibrous web described in Example 1, no one-way valve characteristics are obtained Aqueous fluid flows readily in both directions.

CONTROL EXAMPLE 3

Figure 4:
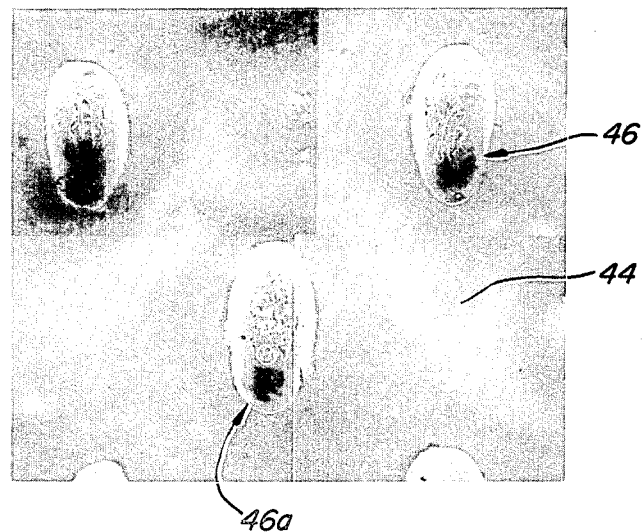
FIG. 4 is a scanning electron micrograph of a facing made in accordance with Surowitz, U.S. Pat. No. 3,307,545, shown at a magnification of 70×.
Figure 5:
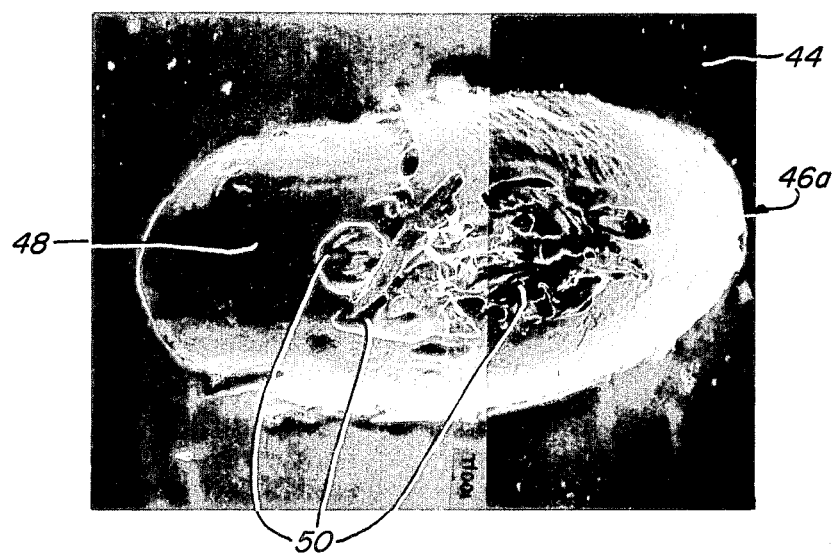
FIG. 5 is a further enlarged scanning electron micrograph of a portion of the facing of FIG. 4, shown at a magnification of 170×.

Scanning electron micrographs of a product made in accordance with the teachings of Surowitz in U.S. Pat. No. 3,307,545 are shown in FIGS. 4 and 5. It is seen that the product has a substantially continuous coating 44 of plastic film, with a plurality of recesses 46. One of the recesses 46a plastic film is shown in greater magnification in FIG. 5. It is seen that in the recess, the plastic film is present as a substantially continuous coating 48 containing a pattern of holes or openings 50. The holes 50 are concentrated in the central (lowest) portion of the recesses 46.

In FIG. 6 there is shown a sanitary napkin 52 which utilizes the absorbent facing material of the invention. The napkin 52 contains an absorbent core 54, which may comprise absorbent fibrous material such as comminuted wood pulp fibers, cotton linters, rayon fibers, cotton staples, and the like. The core 54 of the napkin 52 is enveloped by a layer 56 of the absorbent facing material of the invention. The napkin 52 will also normally contain a fluid impervious layer (not shown) on the side normally worn away from the body.

In FIG. 7, there is shown a disposable diaper 58 which employs the facing material of the invention. The diaper 58 comprises an absorbent core 60, a fluid impervious layer 62, and a layer 64 of the absorbent facing of the invention.

Figure 9:
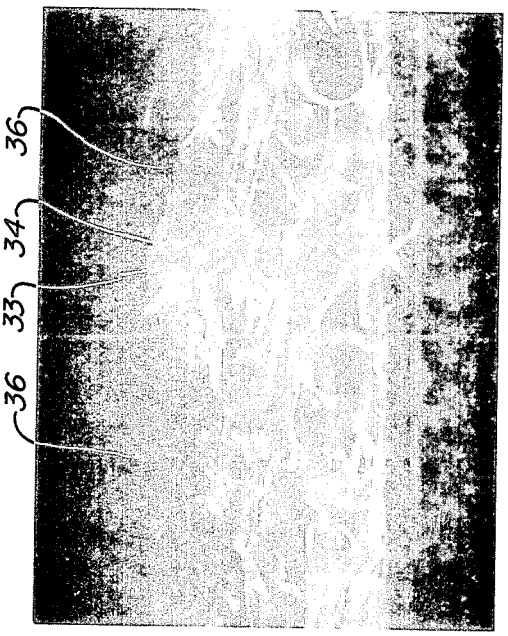
FIGS. 8 and 9 are cross-sectional views at 50× of the Surowitz facing and facing of Example 1, respectively.
Figure 8:
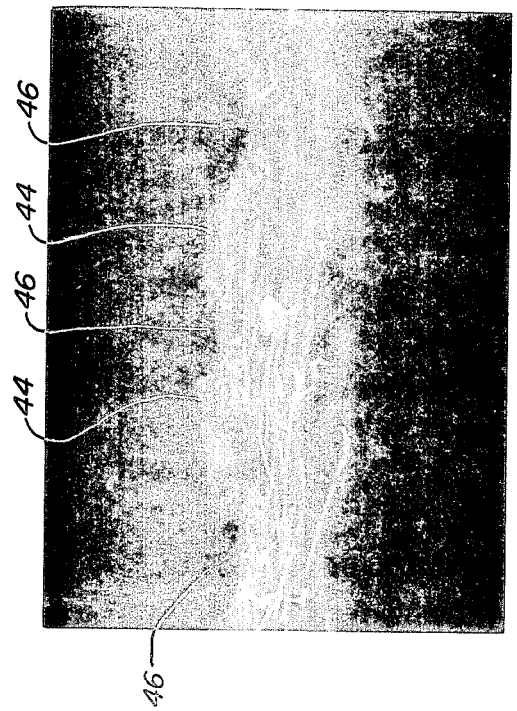
Figure 11:
FIGS. 10 and 11 are top plan views at 20× of the Surowitz facing and the facing of Example 1, respectively.
Figure 10:
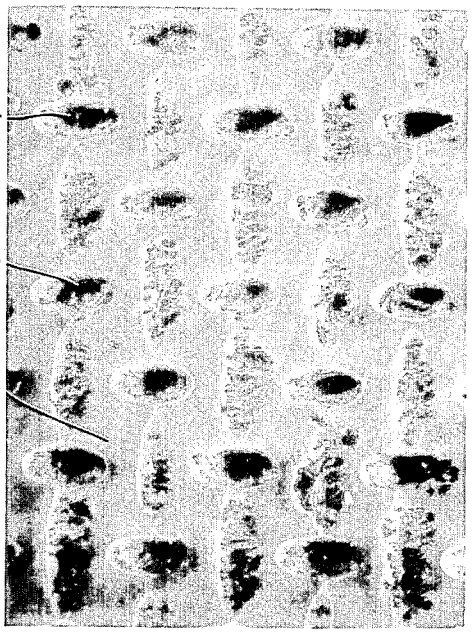

FIGS. 8 through 15 further distinguish the absorbent facing material of the present invention from that of Surowitz in U.S. Pat. No. 3,307,545. FIGS. 8 and 9 depict the cross-sectional views at 50× of the Surowitz facing of FIGS. 4 and 5, and the facing of Example 1, respectively. FIGS. 10 and 11 are top plan views of the Surowitz facing of FIGS. 4 and 5, and the facing of Example 1, respectively. As can be seen in the Surowitz products in FIGS. 8 and 10, the product has a substantially continuous coating of plastic film 44 with a plurality of recesses 46. One of the recesses 46b is shown in greater magnification in FIGS. 12 and 14 and will be described more completely below. In FIGS. 9 and 11, it may be noted that the absorbent facing material 36 of the present invention, and specifically, of Example 1, comprises a fine pattern of continuous areas 34 which lie between and interconnect discontinuous areas 36. As may be seen in both FIGS. 9 and 11, the polymer in the continuous areas comprises in at least substantially continuous coating on the surface of the web, and no part of the continuous coating is recessed down into the web. One of the discontinuous areas 36b is shown in greater magnification in FIGS. 13 and 14 and will be described more completely below.

Figure 13:
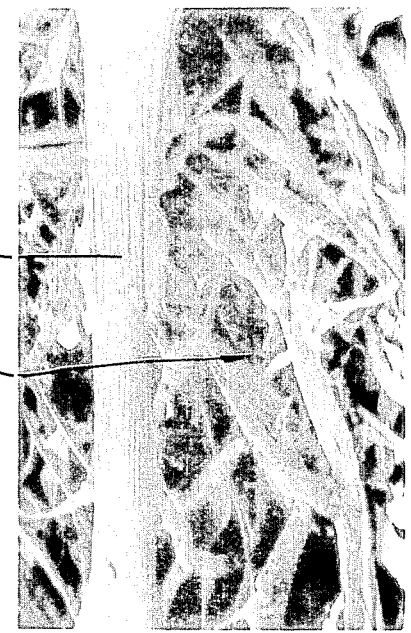
FIGS. 12 and 13 are top perspective views at 100× of the Surowitz facing and the facing of Example 1, respectively.
Figure 12:
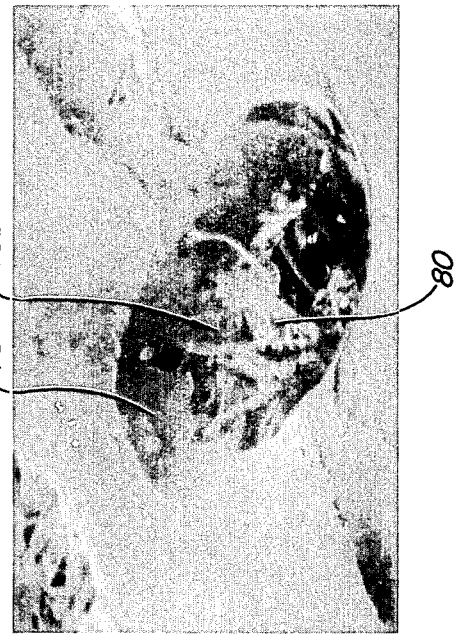
Figure 15:
FIGS. 14 and 15 are enlargements of views 12 and 13, shown at 200×.
Figure 14:
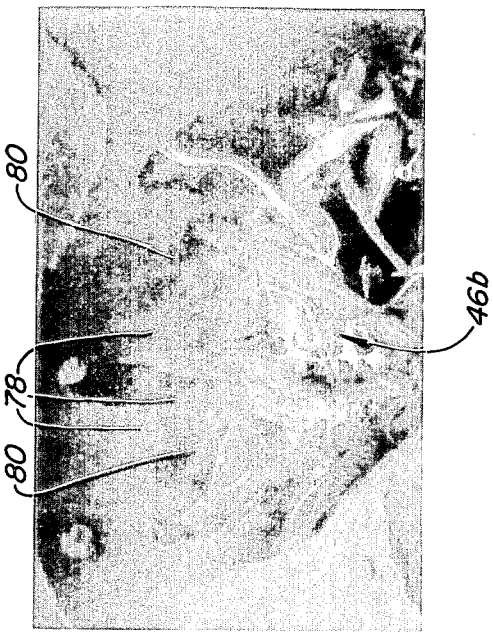

FIGS. 12 and 14 give a top perspective view at 100× and 200×, respectively, of the Surowitz facing shown in FIGS. 4, 5, 8, and 10, and show at greater magnification one of the recesses 46b as seen in FIGS. 12 and 14, the continuous coating of plastic film and the recess extends down into the web, leaving the surface of the web. The plastic film is present in a substantially continuous coating 78 containing a pattern of holes or openings 80 in the central (lowest) portion of the recesses FIGS. 13 and 15 show at greater magnification, one of the discontinuous areas 36a of the absorbent dressing of Example 1. As may be seen in both FIGS. 13 and 15, the polymer in the continuous areas 34 which lie between and interconnect the discontinuous area 36, comprise a substantially continuous coating on the surface of the web, and do not recess into the web. As also shown in FIGS. 13 and 15, the polymer in the discontinuous areas 36a is coated on the individual fibers of the web.

While a sanitary napkin and a disposable diaper have been shown, there are various other types of absorbent products in which the absorbent facing of the invention can be employed. These include tampons, underpads, surgical dressings or bandages, and the like. The absorbent facing of the invention is particularly useful as a surgical dressing or bandage because body fluids pass through it quite readily, but the facing has excellent non-sticking or wound-release properties.

EXAMPLE 3

An absorbent facing was made using the same materials as those described in Example 2, and using the same equipment and substantially the same procedure except that the resilient roll was heated instead of the smooth roll and the pressure at the nip was about 60 pounds per linear inch. The temperature of the resilient roll was about 245° F., and the smooth roll reached a temperature of about 200° F. Excellent absorbent facings were made which had one-way valve characteristics with respect to aqueous liquids, using both ½-mil and ¼-mil polyethylene film.

EXAMPLE 4

Example 3 was repeated using a pressure at the nip of about 5 pounds per linear inch. A good absorbent facing was made.

EXAMPLE 5

Example 4 was repeated except that the fibrous web was a polypropylene fiber web weighing about 4 ounces per square yard, which had been treated to make the fibers hydrophilic. A good absorbent facing was produced.

In Examples 3-5, wherein the resilient roll instead of the smooth roll is heated, lower temperatures than those set forth above in the specification can be used because the heat does not have to pass through the fibrous web.

I claim:

1. Process for producing an absorbent facing material, which process comprises:
   (a) superimposing a thin polymer film and a first web comprising absorbent fibers, to form a second web having said thin polymer film on one face and said first web on the other face;
   (b) heating said second web to a temperature such that said polymer film is formable;
   (c) while said second web is so heated, simultaneously applying shearing and compressive forces to said second web to form said polymer film into a coating on said first web, said coating comprising a fine pattern of continuous areas which lie between and interconnect discontinuous areas, wherein the polymer in the continuous areas comprises an at least substantially continuous coating on the surface of said first web, and wherein most of the polymer in the discontinuous areas is coated on individual fibers underlying said discontinuous areas; and
   (d) cooling the coated web thus formed to cool said polymer below its forming temperature.

2. Process of claim 1 wherein step (b) includes contacting said other face with a heated, continuously moving, uniform surface.

3. Process of claims 1 or 2 wherein step (c) includes contacting said one face with a continuously moving resilient surface having a pattern of continuously arranged recessed areas and discontinuously arranged raised areas disposed uniformly over said resilient surface.

4. Process of claim 1 wherein said process includes passing said second web through the nip between a pair of counter-rotating rolls, the first roll of said pair being in contact with said one face and having a resilient surface that has a pattern of continuously arranged recessed areas and discontinuously arranged raised areas disposed uniformly over said resilient surface, and the second roll of said pair being in contact with said other face, wherein said second roll has a smooth, uniform surface, and wherein at least one of said rolls is heated.

5. The process of claim 4 wherein said first roll is moving at a slightly higher peripheral speed than said second roll.

6. The process of claims 4 or 5 wherein the pressure at said nip is within the range of from about 5 to about 90 pounds per linear inch.

7. The process of claim 4 wherein the polymer is an olefin polymer.

8. The process of claim 7 whrein the polymer film has a thickness of from about ¼ mil to about 1 ¼ mils.

9. The process of claim 4 wherein the first web comprises absorbent papermaking fibers.

10. The process of claim 7 wherein the first web comprises absorbent papermaking fibers.

11. The absorbent facing material produced by the process of claims 1 or 4.

12. An absorbent product having an absorbent core and an absorbent facing material, wherein said absorbent facing material is the absorbent facing of claim 11.

13. The absorbent product of claim 12 wherein said product is a surgical dressing.

14. The absorbent product of claim 12 wherein said product is a sanitary napkin.

15. The absorbent product of claim 12 wherein said product is a disposable diaper.

* * * * *